US010426440B2

(12) United States Patent
Nagae et al.

(10) Patent No.: US 10,426,440 B2
(45) Date of Patent: Oct. 1, 2019

(54) SUBJECT INFORMATION OBTAINING APPARATUS, METHOD FOR OBTAINING SUBJECT INFORMATION, AND PROGRAM

(75) Inventors: Kenichi Nagae, Yokohama (JP); Hirofumi Taki, Kyoto (JP); Takuya Sakamoto, Kyoto (JP); Toru Sato, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 227 days.

(21) Appl. No.: 14/342,342

(22) PCT Filed: Aug. 29, 2012

(86) PCT No.: PCT/JP2012/072525
§ 371 (c)(1),
(2), (4) Date: Feb. 28, 2014

(87) PCT Pub. No.: WO2013/032021
PCT Pub. Date: Mar. 7, 2013

(65) Prior Publication Data
US 2014/0213902 A1 Jul. 31, 2014

(30) Foreign Application Priority Data
Sep. 2, 2011 (JP) ................... 2011-191415

(51) Int. Cl.
*A61B 8/08* (2006.01)
*G01S 7/52* (2006.01)
*G01S 15/89* (2006.01)

(52) U.S. Cl.
CPC ............ *A61B 8/485* (2013.01); *A61B 8/5223* (2013.01); *G01S 7/52028* (2013.01); *G01S 7/52047* (2013.01); *G01S 15/8977* (2013.01)

(58) Field of Classification Search
CPC .......... A61B 8/485; A61B 8/5223; A61B 8/08
See application file for complete search history.

(56) References Cited

U.S. PATENT DOCUMENTS 6,057,927 A * 5/2000 Levesque ............... G01B 11/18
356/432
6,903,634 B2 * 6/2005 Chang .................... H01P 7/082
333/235

(Continued)

FOREIGN PATENT DOCUMENTS

CN 85100528 A 5/1986
CN 101879077 A 11/2010

(Continued)

OTHER PUBLICATIONS

Taki, H., et al. "Hight Resolution Medical Acoustic Vascular Imaging Using Frequency Domain Interferometry".

(Continued)

*Primary Examiner* — Angela M Hoffa
(74) *Attorney, Agent, or Firm* — Canon U.S.A., Inc. IP Division

(57) ABSTRACT

A subject information obtaining apparatus includes: a plurality of conversion elements configured to receive an elastic wave and convert the elastic wave into a plurality of received signals, a storage unit configured to store a plurality of reference signals corresponding to shapes of the object inside a subject, and an FDI adaptive processing unit configured to execute the FDI method and the adaptive signal processing using the plurality of received signals and two or more reference signals among the plurality of reference signals, in order to obtain two or more power intensity distributions for the two or more reference signals.

16 Claims, 8 Drawing Sheets

(56) References Cited

U.S. PATENT DOCUMENTS

| | | | |
|---|---|---|---|
| 9,304,191 B2* | 4/2016 | Nagae | G01S 15/8977 |
| 9,367,945 B2* | 6/2016 | Nagae | G01S 7/52047 |
| 9,435,881 B2* | 9/2016 | Nagae | G01S 7/52047 |
| 9,442,187 B2* | 9/2016 | Nagae | G01S 7/52047 |
| 9,585,629 B2* | 3/2017 | Nagae | A61B 8/085 |
| 9,683,971 B2* | 6/2017 | Taki | G01N 29/24 |
| 9,709,675 B2* | 7/2017 | Taki | G01S 7/52 |
| 9,757,093 B2* | 9/2017 | Taki | A61B 8/14 |
| 10,048,373 B2* | 8/2018 | Taki | G01S 7/52 |
| 2002/0176519 A1* | 11/2002 | Chiodini | H04L 27/2675 375/324 |
| 2005/0073457 A1* | 4/2005 | Li | H01Q 3/22 342/368 |
| 2008/0018901 A1* | 1/2008 | Groot | G01B 11/2441 356/450 |
| 2011/0208057 A1* | 8/2011 | Oikawa | A61B 5/0095 600/443 |

FOREIGN PATENT DOCUMENTS

| | | |
|---|---|---|
| JP | 2010183979 A | 8/2010 |
| RU | 2158619 C2 * | 11/2000 |

OTHER PUBLICATIONS

Taki, et al., "High Range Resolution Medical Acoustic Vascular Imaging with Frequency Domain Interferometry", 32nd Annual International Conference of the IEEE EMBS Buenos Aires, Aregentina, Aug. 31-Sep. 4, 2010, pp. 5298-5301.

Taki, et al., "High Resolution Medical Acoustic Vascular Imaging Using Frequency Domain Interferometry", Proceedings of the Ninth IASTED International COnfernece Visualization, Imaging, and Image Processing (VIIP 2009) Jul. 13-15, 2009, Cambridge UK pp. 7-13.

* cited by examiner

Power Intensity Distribution P0

Power Intensity Distribution P4

Power Intensity Distribution P10

SUBJECT INFORMATION OBTAINING APPARATUS, METHOD FOR OBTAINING SUBJECT INFORMATION, AND PROGRAM

CROSS REFERENCE TO RELATED APPLICATIONS

This application is a U.S. National Stage of International application No. PCT/JP2012/072525 filed on Aug. 29, 2012 which claims priority from Japanese Patent Application JP 2011-191415 filed on Sep. 2, 2011, the disclosures of which are hereby incorporated by reference herein in their entirety.

TECHNICAL FIELD

The present invention relates to a subject information obtaining apparatus, a method for obtaining subject information, and a program, and, more particularly, to a technique for obtaining subject information by transmitting an elastic wave to a subject and by receiving a wave reflected from the inside of the subject.

BACKGROUND ART

In general, in an ultrasonic diagnostic apparatus as a subject information obtaining apparatus, the spatial resolution in the depth direction when image data is formed by a pulse-echo method can be represented by an expression $(n\lambda)/2$, where $\lambda$ denotes the wavelength of an ultrasonic wave and n denotes the number of waves transmitted. For example, when two wavelengths of an ultrasonic wave having a center frequency of 12 MHz are transmitted, the spatial resolution in the depth direction is about 0.13 mm.

The pulse-echo method will be described. First, when an ultrasonic pulse (an elastic wave) has been transmitted to a subject, an ultrasonic wave is reflected and comes back in accordance with differences in acoustic impedance inside the subject. Next, the reflected wave is received and image data is generated using a received signal of the reflected wave. Typically, an envelope of the received signal is obtained and converted into values of brightness, in order to generate the image data. By repeating transmission and reception of an ultrasonic wave in a plurality of directions or positions in the subject, brightness information on a plurality of scan lines in a direction in which the ultrasonic waves have been transmitted and received can be obtained. By arranging the brightness information on the plurality of scan lines, the inside of the subject can be imaged.

In general, in the ultrasonic diagnostic apparatus, a plurality of conversion elements that convert ultrasonic waves into electrical signals are used and time differences are provided between the waveforms of signals received by the conversion elements, so that the inside of the subject is focused both in the transmission and the reception.

Although it is possible to realize a spatial resolution of about 0.13 mm in the depth direction by using the pulse-echo method, higher spatial resolution is required. For example, if the layer structure of the blood vessel walls of a carotid artery can be observed in more detail, it is possible to contribute to early detection of arteriosclerosis or the like.

As techniques for improving the spatial resolution in the depth direction, a frequency-domain interferometry (FDI) method and a Capon method, which is a type of adaptive signal processing, are used in NPL 1, in order to present results of imaging of the layer structure of blood vessel walls. By using the FDI method and the Capon method for received signals, it is possible to further improve the spatial resolution in the depth direction (scan line direction). However, a plurality of reflection layers are supposed to exist in a range (processing range) of a signal in the depth direction that has been cut out in order to execute the processing of the FDI method. In addition, it is likely that a plurality of waves reflected from reflection layers that are located close to one another have a high correlation. It is known that if the adaptive signal processing such as the Capon method is directly adopted for received signals of a plurality of such reflected waves that have a high correlation, unexpected effects such as cancellation of a desired signal can be produced. The effects produced by signals (coherent interference waves) that have a correlation can be reduced by using a frequency-averaging technique, and the FDI method and the Capon method can be adopted for the received signals of reflected waves.

Furthermore, when the frequency-averaging technique is adopted for a received signal of an elastic wave having a wide frequency band, such as a pulse wave, whitening of the received signal is performed using a reference signal. In PTL 1, an apparatus is described in which a plurality of standard signals for forming a reference signal are combined using a certain interpolation ratio and an obtained signal (an operational reference signal) is used as the reference signal.

CITATION LIST

Patent Literature

PTL 1 Japanese Patent Laid-Open No. 2010-183979

Non Patent Literature

NPL 1 Hirofumi Taki, Kousuke Taki, Takuya Sakamoto, Makoto Yamakawa, Tsuyoshi Shiina, and Toru Sato: Conf Proc IEEE Eng Med Biol Soc. 2010; 1: 5298-5301

SUMMARY OF INVENTION

In PTL 1, as illustrated in FIG. 9, a polyethylene sheet 50 and an acryl plate 51 are disposed in water 52 to form an interface 71 between the water 52 and the polyethylene sheet 50 and an interface 72 between the polyethylene sheet 50 and the acryl plate 51. A reference signal is created using received signals of waves reflected from this plurality of reflection interfaces when an ultrasonic wave has been transmitted from a probe 60. That is, in PTL 1, a reference signal created using received signals of waves reflected of a plurality of reflection interfaces whose materials (hardness) are different from each other is used for the FDI method and the adaptive signal processing. By executing the FDI method and the adaptive signal processing using such a reference signal, it is possible to improve the spatial resolution of an obtained image compared to when a received signal of a wave reflected from a single reflection interface is used as a reference signal. However, even when the FDI method and the adaptive signal processing are executed using the reference signal according to PTL 1, an image can deteriorate depending on an object to be measured.

The present invention provides a technique for making it possible to obtain image data whose spatial resolution is improved when the FDI method and the adaptive signal processing are adopted.

Solution to Problem

A subject information obtaining apparatus in the present invention is a subject information obtaining apparatus that transmits an elastic wave to a subject, that receives the elastic wave reflected from an object inside the subject, and that obtains information regarding the subject. The subject information obtaining apparatus includes a plurality of conversion elements configured to receive the elastic wave and convert the elastic wave into a plurality of received signals, a storage unit configured to store a plurality of reference signals corresponding to shapes of the object, and a frequency-domain interferometry adaptive processing unit configured to execute a frequency-domain interferometry method and adaptive signal processing using the plurality of received signals and two or more reference signals among the plurality of reference signals, in order to obtain two or more power intensity distributions for the two or more reference signals.

A method for obtaining subject information in the present invention is a method for obtaining subject information in which an elastic wave is transmitted to a subject, the elastic wave reflected from an object inside the subject is received, and information regarding the subject is obtained. The method includes a step of executing a frequency-domain interferometry method and adaptive signal processing using a plurality of received signals output from a plurality of conversion elements that have received the elastic wave and two or more reference signals among a plurality of reference signals corresponding to shapes of the object, in order to obtain two or more power intensity distributions for the two or more reference signals.

Advantageous Effects of Invention

According to the present invention, by using reference signals according to the shapes of objects inside a subject, the effects of the FDI method and the adaptive signal processing can be enhanced, and image data whose spatial resolution is improved can be obtained.

DESCRIPTION OF EMBODIMENTS

Figure 1:
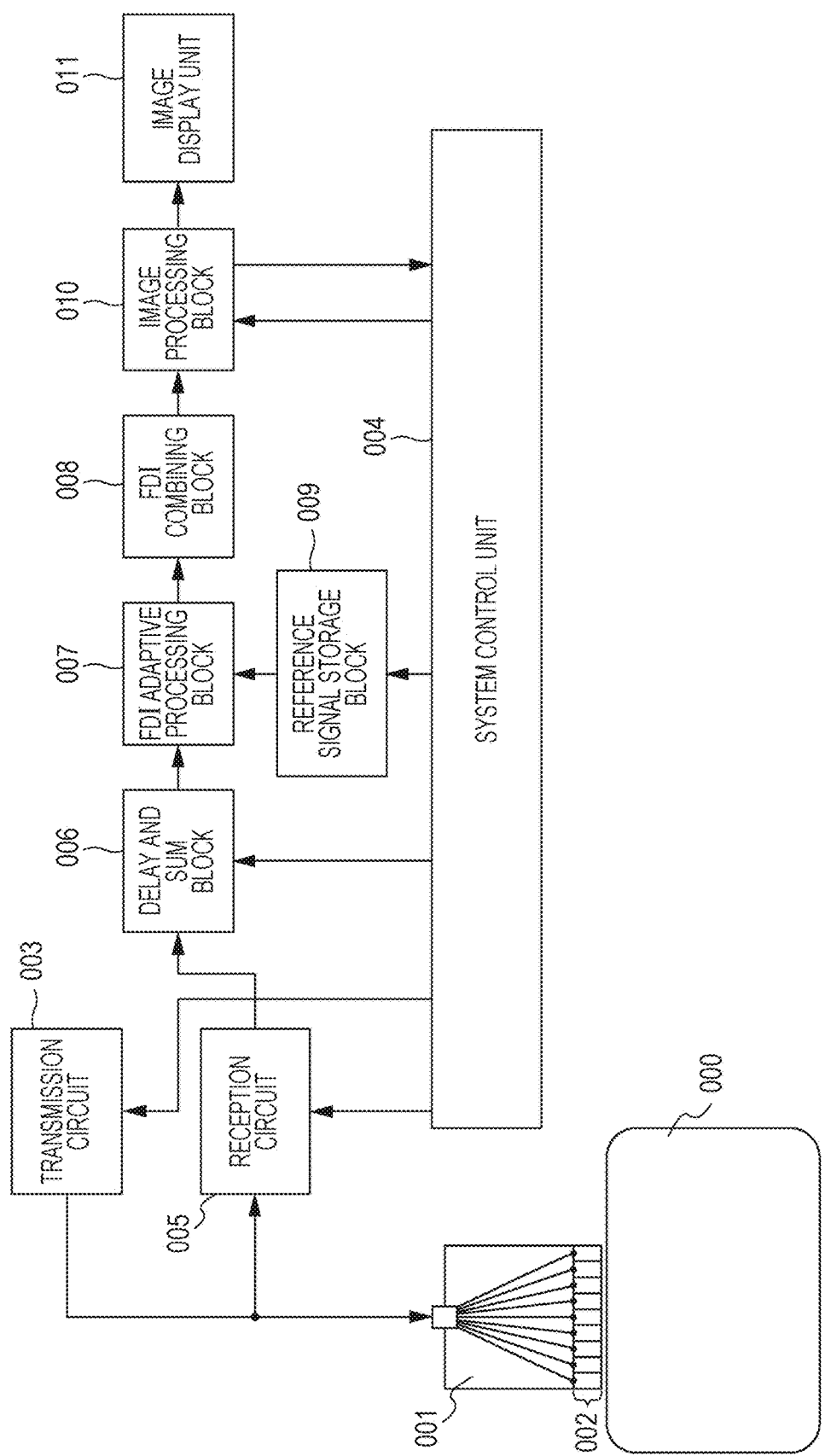
FIG. 1 is a schematic diagram illustrating the systematic overview of a subject information obtaining apparatus to which the present invention can be applied.

The inventors have noticed that an image can deteriorate when there is a difference between the waveform of a received signal of a reflected wave that is actually received during measurement of a subject and the waveform of a reference signal. The inventors have also noticed that even with the same object, the frequency spectrum and the phase of a reflected wave can change depending on the shape of the object, that is, the inclination and the size of the object, and accordingly a difference is caused between the waveform of a received signal of a reflected wave that is actually received and the waveform of a reference signal, thereby deteriorating an image.

For example, when a received signal of a wave reflected from an interface that lies at right angles to a scan line is used as a reference signal, the difference between the waveform of the received signal of the wave reflected from the interface and the waveform of a reference signal increases as an angle between the interface (an object) located inside a subject and the scan line deviates from 90°. Due to this difference between the waveforms, an effect of improving the spatial resolution produced by an FDI method and adaptive signal processing can become difficult to obtain and the value of power can change. Accordingly, this can result in deterioration of an image.

Therefore, in the present invention, a plurality of reference signals corresponding to the shapes (the angles of objects relative to a scan line, the sizes of the objects, the radii of curvature of the objects, and the like) of the objects (reflection interfaces and reflection bodies) inside a subject are prepared in advance. The FDI method and the adaptive signal processing are executed using such a plurality of reference signals.

In the present invention, an elastic wave is typically an ultrasonic wave and includes an elastic wave called a sonic wave, an ultrasonic wave, or an acoustic wave. A subject information obtaining apparatus in the present invention includes an apparatus that transmits an elastic wave to a subject, receives a wave (the reflected elastic wave) reflected from the inside of the subject, and obtains subject information as image data. The obtained subject information is information that reflects differences in acoustic impedance between tissues inside the subject. In the present invention, a scan line refers to a virtual line formed in a direction in which an elastic wave transmitted from a probe propagates.

Embodiments of the present invention will be described hereinafter with reference to the drawings. The same components are given the same reference numerals, and description thereof is omitted.

Basic Configuration of Subject Information Obtaining Apparatus

Figure 2:
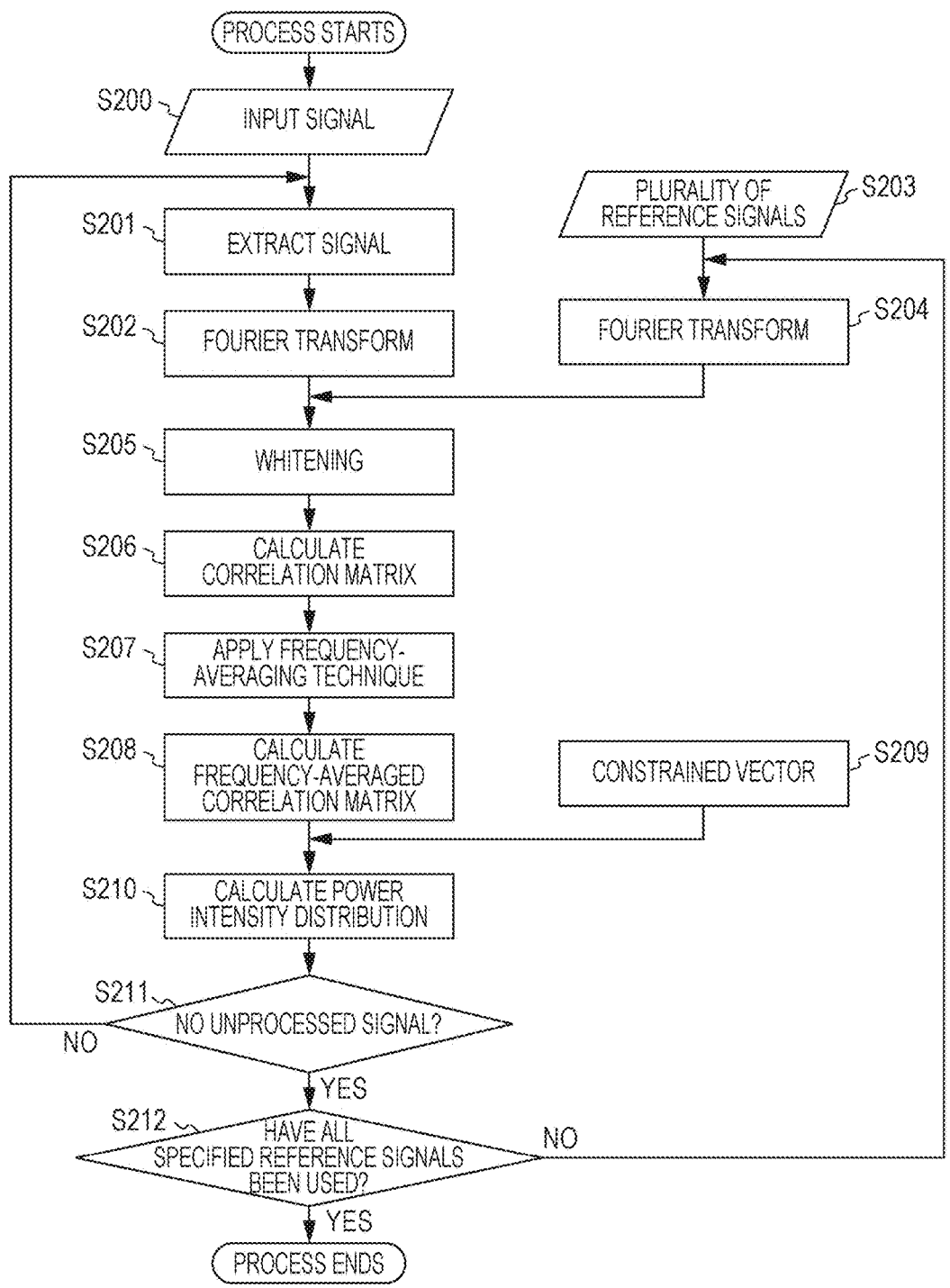
FIG. 2 is a flowchart illustrating processing executed inside an FDI adaptive processing block.

The configuration of a subject information obtaining apparatus to which the present invention can be applied and details of a process when the FDI method and the adaptive signal processing are used will be described with reference to FIGS. 1 and 2. FIG. 1 is a schematic diagram illustrating the systematic overview of a subject information obtaining apparatus in the present invention. The subject information obtaining apparatus according to an embodiment includes a probe 001 having a plurality of conversion elements 002, a reception circuit 005, a transmission circuit 003, a delay and sum block 006, an FDI adaptive processing block 007, and a reference signal storage block 009. An FDI combining block 008, an image processing block 010, and a system control unit 004 are also included.

In the present invention, the delay and sum block 006 corresponds to a delay and sum unit, the FDI adaptive processing block 007 corresponds to an FDI adaptive processing unit, the reference signal storage block 009 corresponds to a storage unit, and the image processing block 010 corresponds to an image processing unit. The FDI combining block 008 corresponds to an output unit that combines a plurality of power intensity distributions or selects one of the plurality of power intensity distributions and that outputs a selected power intensity distribution to be used to obtain subject information. In addition, a processing apparatus is configured at least by the delay and sum block 006, the FDI adaptive processing block 007, and the reference signal storage block 009, and the processing apparatus can include the FDI combining block 008 as necessary. In the present invention, an obtained power intensity distribution indicates subject information that reflects differences in acoustic impedance between tissues inside a subject.

The transmission circuit 003 generates a transmission signal having a delay time and an amplitude according to a target position and a target direction in accordance with a control signal from the system control unit 004. The transmission signal is converted into an elastic wave by the plurality of conversion elements 002, and the elastic wave is transmitted from the probe 001 to the subject. The elastic wave (reflected wave) reflected by an object (a reflection interface or a reflection body) inside a subject 000 is received by the plurality of conversion elements 002 and converted into a plurality of received signals. The received signals are input to the reception circuit 005.

The reception circuit 005 amplifies the plurality of received signals and converts the plurality of received signals into a plurality of digital signals (digitized received signals). In the present invention, not only analog received signals output from the conversion elements 002 but also amplified signals and signals subjected to processing such as digital conversion are referred to as received signals. The plurality of digital signals output from the reception circuit 005 are input to the delay and sum block 006.

The delay and sum block 006 executes a delay process on the plurality of digital signals in accordance with a direction in which or a position at which the elastic wave has been transmitted and sums the plurality of digital signals, that is, executes a delay and sum process. Thus, the signals (scan line signals) after the delay and sum process are input to the FDI adaptive processing block 007. A scan line signal indicates a signal at each depth of each scan line, and a plurality of scan line signals are arranged on a single scan line. In a B-mode image displayed on a general ultrasonic apparatus, envelopes of these scan line signals are arranged for a plurality of scan lines.

The plurality of scan line signals for each scan line output from the delay and sum block 006 and a plurality of reference signals output from the reference signal storage block 009 are input to the FDI adaptive processing block 007. The FDI adaptive processing block 007 then obtains a plurality of power intensity distributions corresponding to the plurality of reference signals. With respect to the plurality of reference signals output from the reference signal storage block 009, not all the reference signals stored in the reference signal storage block 009 need not be input to the FDI adaptive processing block 007. Two or more reference signals can be selected by an instruction issued by the system control unit 004. That is, a power intensity distribution can be obtained for each of the two or more reference signals. The plurality of power intensity distributions are then input to the FDI combining block 008.

The FDI combining block 008 generates a combined power intensity distribution by executing a combining process such as an averaging process using the plurality of input power intensity distributions, and outputs the combined power intensity distribution to the image processing block 010. However, in the present invention, an appropriate one of the plurality of input power intensity distributions may be selected and may be output to the image processing block 010, instead of outputting the combined power intensity distribution generated by the combining process to the image processing block 010. That is, the output unit in the present invention may function as a combining unit that executes the combining process using the plurality of power intensity distributions or may function as a selection unit that selects a power intensity distribution whose spatial resolution is high from among the plurality of power intensity distributions. Image data indicating subject information is generated in the end on the basis of the power intensity distribution output from the output unit.

The image processing block 010 executes various types of image processing such as smoothing and edge reinforcement on the input combined power intensity distribution as necessary, and outputs brightness data (image data) to an image display unit 011. The image display unit 011 displays the input brightness data. The image display unit 011 may be provided separately from the subject information obtaining apparatus in the present invention.

Alternatively, in the present invention, the plurality of power intensity distributions generated by the FDI adaptive processing block 007 may be output to the image processing block 010. In this case, the image processing block 010 generates a plurality of pieces of brightness data based on the plurality of power intensity distributions and causes the image display unit 011 to display the plurality of pieces of brightness data. Thus, by displaying a plurality of power intensity distribution images, a measurer (user) can see differences between the images and select a desired power intensity distribution image whose spatial resolution is high.

Flow of FDI Adaptive Processing to which Present Invention can be Applied

Processing executed inside the FDI adaptive processing block 007 will be described hereinafter. First, the concepts of the FDI method and the adaptive signal processing will be described, and then a detailed processing flow will be described.

The FDI method is a method in which the received signals are divided in terms of frequencies and the phases of the divided signals are changed in accordance with target positions, in order to estimate the received power at the target positions. The amount of change in the phase can be predetermined on the basis of the product of the distance from a certain reference position to a target position and the number of waves corresponding to the frequency.

In the adaptive signal processing, processing parameters are adaptively changed in accordance with the received signals. A Capon method, which is a type of the adaptive signal processing, is a method in which the plurality of input signals are processed such that power is minimized while sensitivity relative to the target positions remains the same. That is, in the combination between the FDI method and the adaptive signal processing, the received power at the target positions is estimated using, for the received signals that have been divided into frequency components, not the predetermined amount of change in the phase and weight but the amount of change in the phase and weight that have been calculated in accordance with the signals through the adaptive signal processing.

Next, processing executed in the FDI adaptive processing block 007 will be described hereinafter with reference to FIG. 2. The FDI adaptive processing block 007 receives scan line signals output from the delay and sum block 006 as input signals (S200). Next, a signal corresponding to a period of time to be processed at a time, that is, a signal corresponding to a processing range, is extracted from the plurality of scan line signals (S201). Here, in the processing executed by the FDI adaptive processing block 007, not only a signal corresponding to a processing range may be extracted from the plurality of scan line signals on a single scan line, but also processing such as weighting may be performed on each scan line signal.

Next, the extracted signal is subjected to a Fourier transform and divided into frequency components (Xs1, Xs2, Xs3 . . . , and XsN) (S202). On the other hand, a plurality of reference signals are input to the FDI adaptive processing block 007 from the reference signal storage block 009 (S203). The FDI adaptive processing block 007 then executes a Fourier transform on one of the plurality of reference signals and divides the reference signal into frequency components (Xr1, Xr2, Xr3 . . . , and XrN) (S204).

Next, the FDI adaptive processing block 007 executes a whitening process using an expression (1) (S205).

[Math. 1]

$$X_{wk} = \frac{X_{sk} X_{rk}^*}{|X_{rk}|^2 + \eta} \quad (1)$$

Here, $X_{wk}$ (k=1, 2 . . . , and N) denotes frequency components after the whitening process, $\eta$ denotes a constant term used for stabilization, and * denotes a complex conjugate. Next, a correlation matrix R is calculated using a vector X composed of the frequency components subjected to the whitening process (S206).

$$X = [X_{W1}, X_{W2} \ldots , X_{WN}]^T \quad (2)$$

$$R = XX^{T*} \quad (3)$$

Here, T denotes a transpose. The correlation matrix R is a matrix having a size of N×N. Next, a frequency-averaging technique is used in which submatrices are extracted from the correlation matrix R and averaged (S207).

[Math. 2]

$$R' = \frac{1}{M} \sum_{m=1}^{M} R_m \quad (4)$$

$$R_{mij} = X_{W(i+m-1)} X_{W(j+m-1)}^* \quad (5)$$

R' denotes a frequency-averaged correlation matrix and $R_m$ denotes the submatrices of the correlation matrix R having $R_{mij}$ as elements. Thus, the frequency-averaged correlation matrix R' is calculated (S208).

Next, a constrained vector C is input to the FDI adaptive processing block 007 (S209). The constrained vector C is a vector that changes in accordance with a position r within the processing range and defined by the following expression (6):

$$C = [\exp(jk_1 r), \exp(jk_2 r) \ldots , \exp(jk_{(N-M+1)} r)] \quad (6)$$

A power intensity distribution P(r) within the processing range is calculated using the frequency-averaged correlation matrix R' and the constrained vector C (S210).

[Math. 3]

$$P(r) = \frac{1}{C^T \cdot (R' + \eta' E)^{-1} c} \quad (7)$$

$\eta'E$ denotes a diagonal matrix added to stabilize calculation of an inverse matrix.

Next, if there is an unprocessed signal among the input signals, the process returns to the extraction of a signal (S201) and is repeated (S211). If there is no unprocessed signal among the input signals, the process proceeds to a judgment as to whether or not the process has been performed using all the plurality of specified reference signals (S212). If all the plurality of specified reference signals have been used, the process ends, and if there is a specified reference signal that has not been used among the plurality of specified reference signals, a Fourier transform is performed on a next reference signal (S204), and the process is repeated.

As described above, the FDI adaptive processing block 007 executes the FDI method and the adaptive signal processing (here, the Capon method is used) using the plurality of scan line signals output from the delay and sum block 006 and the plurality of reference signals output from the reference signal storage block 009 as input signals. As a result, a plurality of power intensity distributions corresponding to the plurality of reference signals are output.

Plurality of Reference Signals

The necessity of using the plurality of reference signals will be described hereinafter. As described above, depending on the shape (the angle of an object relative to a scan line, the size of the object, the radius of curvature of the object, and the like) of the object that reflects an elastic wave, the waveform of a received signal of a reflected wave received by the probe 001 varies. For example, a frequency characteristic $F_L(\omega)$ of a reflected wave when a thin wire is used as an object and an elastic wave transmitted from one conversion element is reflected by the thin wire can be represented by the following expression (8):

[Math. 4]

$$|F_L(\omega)|^2 = \frac{(B/4)\Delta S^2 k^4 (\sigma^2/(2f))^4 \pi}{\{(k/f)^2 + (\sigma^2 k^2/(2f^2))^2\}^{1/2}} \quad (8)$$

In addition, a frequency characteristic $F_F(\omega)$ of a reflected wave when a thin film is used as an object and an elastic wave transmitted from one conversion element is reflected by the thin film can be represented by the following expression (9):

[Math. 5]

$$|F_F(\omega)|^2 = \frac{(B/4)\Delta F^2 k^4 (\sigma^2/(2f))^4 \pi^2}{(k/f)^2 + (\sigma^2 k^2/(2f^2))^2} \quad (9)$$

Here, $\omega$ denotes the frequency of each received signal, B denotes the reflectivity relative to a normal incident wave (a transmission wave that is perpendicularly incident on an object), $\Delta S$ denotes the cross-section of the thin wire, $\Delta F$ denotes the thickness of the thin film, k denotes the number of waves, $\sigma$ denotes the radius of one conversion element, and f denotes the curvature of one conversion element.

As described above, the frequency characteristic of a reflected wave varies depending on the type of object. Therefore, when the FDI method and the adaptive signal processing have been performed using only one type of reference signal waveform for various waveforms of received signals of reflected waves, differences between the waveforms of the received signals of the reflected waves and the waveforms of the reference signals are caused. The differences between the waveforms cause a decrease in the effect of improving the spatial resolution and changes in power, thereby resulting in deterioration of an image.

In the present invention, a plurality of reference signals corresponding to the shapes of objects are prepared in advance and the FDI method and the adaptive signal processing are performed using the plurality of reference signals, in order to enable processing according to various elastic waves that have propagated through a subject. That is, a power intensity distribution for each reference signal can be obtained. In the present invention, the "shapes of objects" include the angles of the objects relative to a scan line, the sizes of the objects, and the radii of curvature of the objects. In addition, although the processing based on the Capon method has been described as the adaptive signal processing in the above description, the same effects can be obtained by using other types of adaptive signal processing such as multiple signal classification (MUSIC) and estimation of signal parameters via rotational invariant techniques (ESPRIT).

Subject information obtaining apparatuses according to the embodiments of the present invention will be described in detail hereinafter with reference to the drawings. The same components are basically given the same reference numerals, and description thereof is omitted.

First Embodiment

A subject information obtaining apparatus according to the present embodiment is an apparatus having the same configuration as the apparatus illustrated in FIG. 1. In the present embodiment, first, an example of a plurality of reference signals stored in the reference signal storage block 009 and processing executed by the FDI adaptive processing block 007 will be specifically described. Since processing executed until a plurality of power intensity distributions are obtained is basically the same as the flow illustrated in FIG. 2, processing after the FDI combining block 008 will be described in detail.

In the present embodiment, as a reference signal, a received signal of a wave reflected from a known interface (an interface prepared separately from a subject) is obtained in advance. As the interface, for example, an interface between gelatin and agar may be used. In the following description, cases will be described in which an interface at an angle of 0° relative to a reference plane (a plane perpendicular to the propagation direction (scan line direction) of an elastic wave transmitted from or received by the probe 001), that is, an interface parallel to the reference plane, is prepared, in which an interface at an angle of 4° relative to the reference plane is prepared, and in which an interface at an angle of 10° relative to the reference plane is prepared.

Here, a signal obtained by performing delay and sum on a received signal of a wave reflected from the interface parallel to the reference plane is denoted by $Xr\_0$. A signal obtained by performing delay and sum on a received signal of a wave reflected from the interface at an angle of 4° relative to the reference plane is denoted by $Xr\_4$, and a signal obtained by performing delay and sum on a received signal of a wave reflected from the interface at an angle of 10° relative to the reference plane is denoted by $Xr\_10$. The reference signal storage block 009 according to the present embodiment stores at least the plurality of reference signals $Xr\_0$, $Xr\_4$, and $Xr\_10$. The reference signal storage block 009 may store reference signals other than the reference signals $Xr\_0$, $Xr\_4$, and $Xr\_10$. The plurality of reference signals output from the reference signal storage block 009 can be selected by an instruction issued by the system control unit 004, and the reference signal storage block 009 outputs two or more reference signals.

In the present embodiment, a plurality of scan line signals output from the delay and sum block 006 and the plurality of reference signals ($Xr\_0$, $Xr\_4$, and $Xr\_10$) output from the reference signal storage block 009 are input to the FDI adaptive processing block 007. The FDI adaptive processing block 007 executes the FDI method and the adaptive signal processing illustrated in FIG. 2 using the plurality of reference signals ($Xr\_0$, $Xr\_4$, and $Xr\_10$), and outputs a plurality of power intensity distributions (P0, P4, and P10) corresponding to the reference signals ($Xr\_0$, $Xr\_4$, and $Xr\_10$), respectively.

Figure 3A:
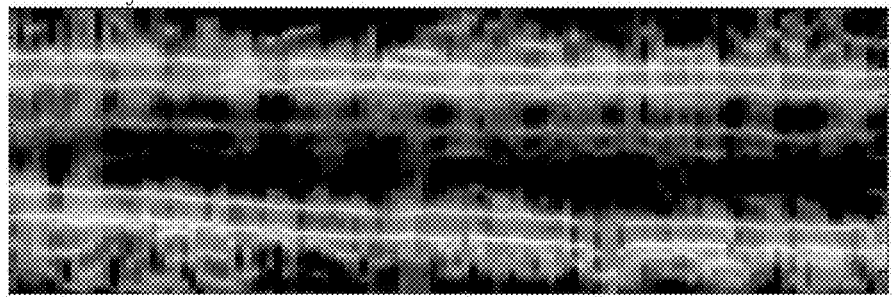
FIGS. 3A to 3C are diagrams illustrating power intensity distributions that use different reference signals.
Figure 3B:
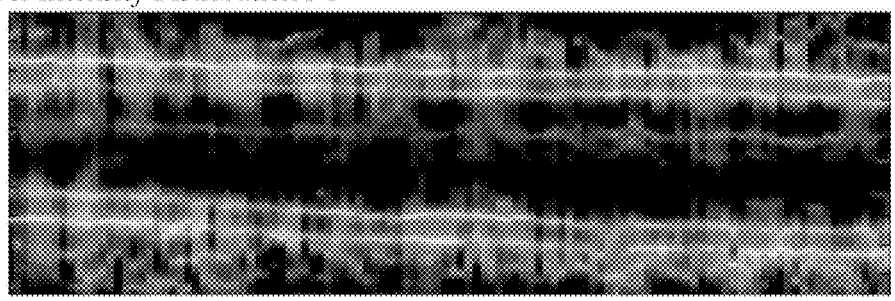
Figure 3C:
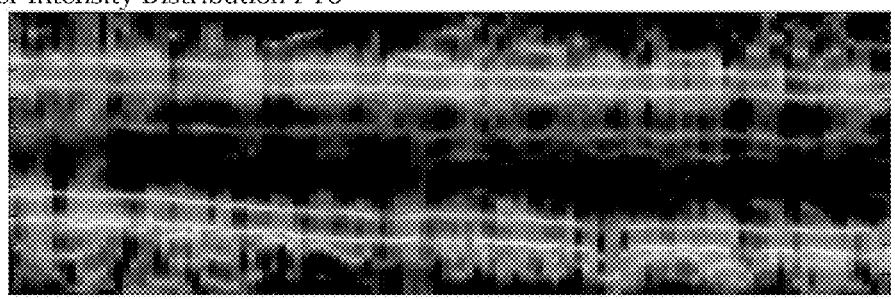
Figure 4:
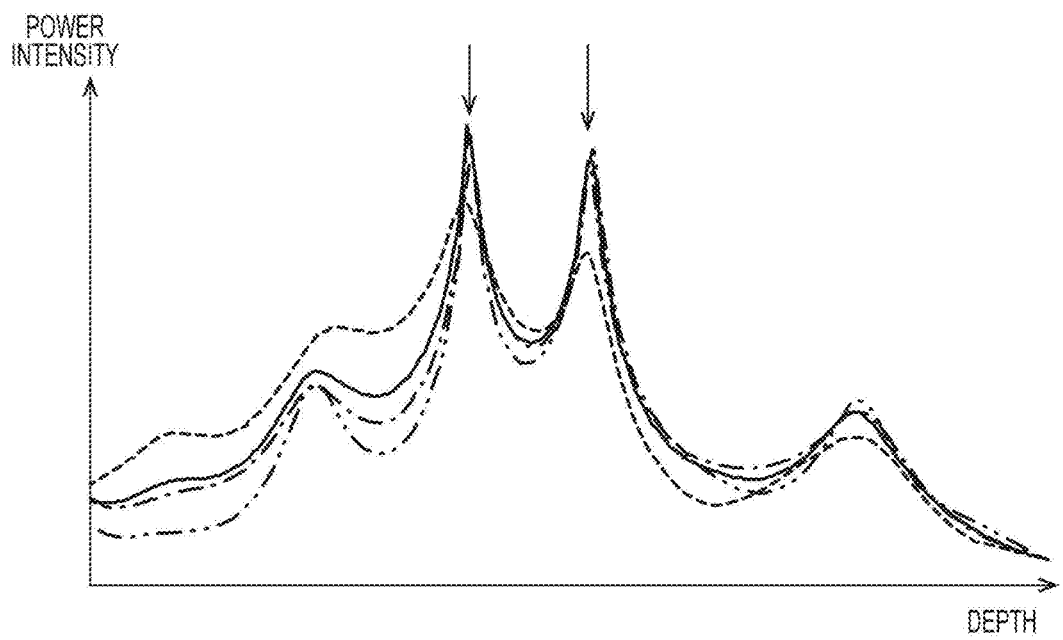
FIG. 4 is a graph obtained by extracting part of a plurality of power intensity distributions and by plotting the part.

FIGS. 3A to 3C illustrate the displayed power intensity distributions (P0, P4, and P10), respectively, that have been subjected to logarithmic compression. It can be seen that the obtained power intensity distribution changes depending on the reference signal used. FIG. 4 is a graph obtained by extracting part of one scan line from each of the power intensity distributions (P0, P4, and P10) illustrated in FIGS. 3A to 3C and by plotting the part of the one scan line. The horizontal axis represents depth (the distance from the probe 001), and the vertical axis represents power intensity. In FIG. 4, a broken line indicates power intensity extracted from the power intensity distribution P0, a dash-dot line indicates power intensity extracted from the power intensity distribution P4, and a dash-dot-dot line indicates power intensity extracted from the power intensity distribution P10.

As can be seen from depths indicated by arrows in FIG. 4, the spatial resolution in the depth direction is higher in the plotted lines (the dash-dot line and the dash-dot-dot line) indicating the power intensity distributions P4 and P10 that use the reference signals $Xr\_4$ and $Xr\_10$, respectively, than in the plotted line (the broken line) indicating the power intensity distribution P0 that uses the reference signal $Xr\_0$. However, the same result is not necessarily obtained in all regions, and the spatial resolution can be higher in the power intensity distribution P0 that uses the reference signal $Xr\_0$ than in the power intensity distributions P4 and P10 that use the reference signals $Xr\_4$ and $Xr\_10$, respectively.

As described above, in the present embodiment, by using the plurality of reference signals based on the waves reflected from the plurality of interfaces whose angles are different from one another for the FDI method and the adaptive signal processing, the spatial resolution can be further improved compared to when only one type of reference signal (for example, $Xr\_0$) is used.

The plurality of power intensity distributions (P0, P4, and P10) output from the FDI adaptive processing block 007 are input to the FDI combining block 008. The FDI combining block 008 executes a combining process on the plurality of input power intensity distributions. An example in which an averaging process is performed will be described hereinafter.

Figure 5:
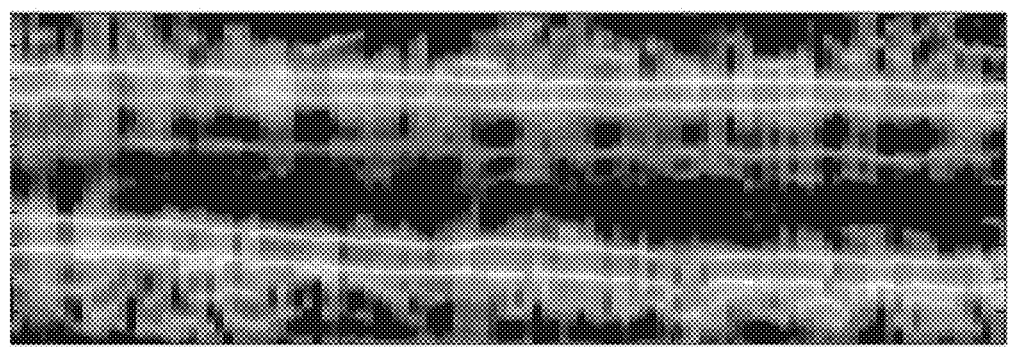
FIG. 5 is a diagram illustrating a combined power intensity distribution obtained in a first embodiment.

FIG. 5 illustrates a displayed power intensity distribution Pave obtained by averaging the plurality of power intensity distributions (P0, P4, and P10) and by performing logarithmic compression. A solid line in FIG. 4 indicates power intensity extracted from the power intensity distribution Pave. Thus, by averaging the plurality of power intensity distributions calculated using the plurality of reference signals, the effect of improving the spatial resolution produced by the FDI method and the adaptive signal processing can be stably obtained. The power intensity distribution Pave obtained by the combining process executed by the FDI combining block 008 is output to the image processing block 010 as a combined power intensity distribution.

The image processing block 010 executes various types of image processing such as smoothing and edge reinforcement on the input combined power intensity distribution and outputs brightness data (image data) to the image display unit 011. The image display unit 011 displays the input brightness data.

By executing such processing, the reference signals corresponding to the shapes of objects can be used when the FDI method and the adaptive signal processing are performed, and therefore the effect of improving the spatial resolution can be further enhanced and stably obtained.

Although the plurality of reference signals corresponding to the angles of objects are used in the present embodiment, a plurality of reference signals corresponding to other types of shapes of objects may be used. For example, the same effect can be expected when received signals of waves reflected from interfaces whose radii of curvature are different from one another, interfaces whose sizes (the sizes of regions that reflect waves) are different from one another, or the like are used as the plurality of reference signals. Furthermore, received signals of waves reflected from a small reflection body (a reflection body smaller than the wavelength of transmitted or received elastic waves) when the size of the reflection body is changed may be used as the plurality of reference signals.

In addition, although the plurality of power intensity distributions output from the FDI adaptive processing block 007 are averaged by the FDI combining block 008 in the present embodiment, the same effect can be obtained by performing a combining process such as weighting and summing the plurality of power intensity distributions. Furthermore, one of the plurality of power intensity distributions may be selected.

Second Embodiment

The method of the combining process executed by the FDI combining block 008 according to the present embodiment is different from that according to the first embodiment. A subject information obtaining apparatus according to the present embodiment has the same configuration as the subject information obtaining apparatus illustrated in FIG. 1. In addition, since the processing method is basically the same as the flow illustrated in FIG. 2, only a processing flow in the FDI combining block 008 will be described hereinafter with reference to FIG. 6.

Figure 6:
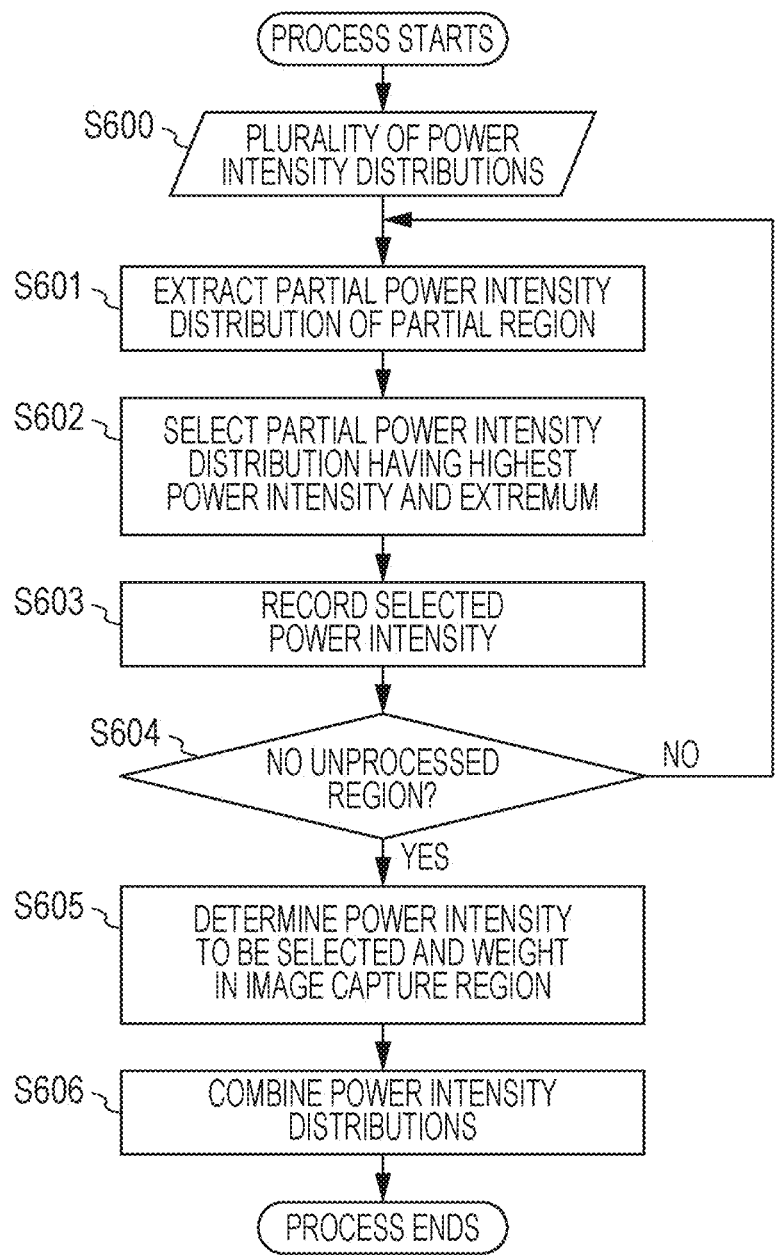
FIG. 6 is a flowchart illustrating the flow of processing executed inside an FDI combining block.

FIG. 6 is a flowchart illustrating the flow of processing executed inside the FDI combining block 008. In S600, the plurality of power intensity distributions (P0, P4, and P10) output from the FDI adaptive processing block 007 are input to the FDI combining block 008. The plurality of power intensity distributions (P0, P4, and P10) are power intensity distributions calculated using the plurality of reference signals (Xr_0, Xr_4, and Xr_10) as in the first embodiment.

In S601, a region (image capture region) inside a subject for obtaining a power intensity distribution is divided into a plurality of partial regions, and a partial power intensity distribution is extracted from one of the plurality of partial regions. At this time, the partial power intensity distribution is extracted from the partial region at the same position from each of the input power intensity distributions (P0, P4, and P10). For example, partial power intensity distributions (P0_1, P4_1, and P10_1) within the same depth range on the same scan line are extracted.

In S602, the plurality of extracted partial power intensity distributions are compared with one another, and a partial power intensity distribution having highest power intensity and an extremum is selected. This selection process will be described with reference to FIG. 7.

Figure 7:
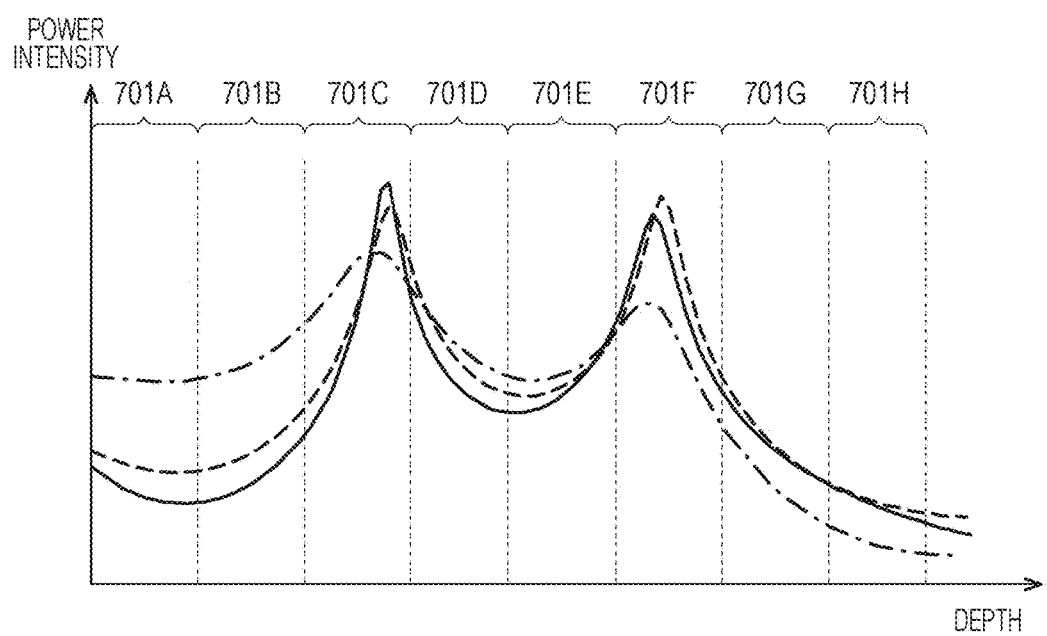
FIG. 7 is a graph obtained by extracting and plotting part of the plurality of power intensity distributions.

FIG. 7 is a graph obtained by extracting a certain region (a region within a certain depth range) on a certain scan line and by plotting a plurality of power intensity distributions. The plurality of power intensity distributions are divided into partial power intensity distributions in a plurality of partial regions (701A to 701H). The partial power intensity distributions in the same partial region are compared with one another, and a partial power intensity distribution having highest power intensity and an extremum in each partial region is selected. For example, a partial power intensity distribution indicated by a solid line in the partial region 701C and a partial power intensity distribution indicated by a broken line in the partial region 701F are selected. The partial regions 701C and 701F correspond to first partial regions in the present invention. In the other partial regions (second partial regions) in the certain region, there is no power intensity distribution having highest power intensity and an extremum, and therefore no selection is made.

In S603, the power intensity distribution selected in each partial region in the above-described manner is recorded. The above-described operation is then repeated until there is no unprocessed region (S604). When there is no unprocessed region, a partial power intensity distribution and a weight to be used in each partial region are determined (S605).

The processing in S605 will be described in detail. With respect to each partial region (the first partial region) in which a partial power intensity distribution has been selected in the processing in S603, the selected partial power intensity distribution is used. With respect to each partial region (the second partial region) in which no selection has been made in S603, a partial power intensity distribution selected in a nearby partial region is used or a plurality of partial power intensity distributions selected in nearby partial regions are weighted and used. In the present embodiment, in S605, a partial power intensity distribution and a weight to be used are determined in each partial region. The weight is obtained by, for example, performing proportional distribution in accordance with distances from a plurality of partial power intensity distributions selected in nearby regions. For example, in each second partial region, a partial power intensity distribution selected in a nearby first partial region may be used to distribute a weight according to a distance from the first partial region.

Figure 8:
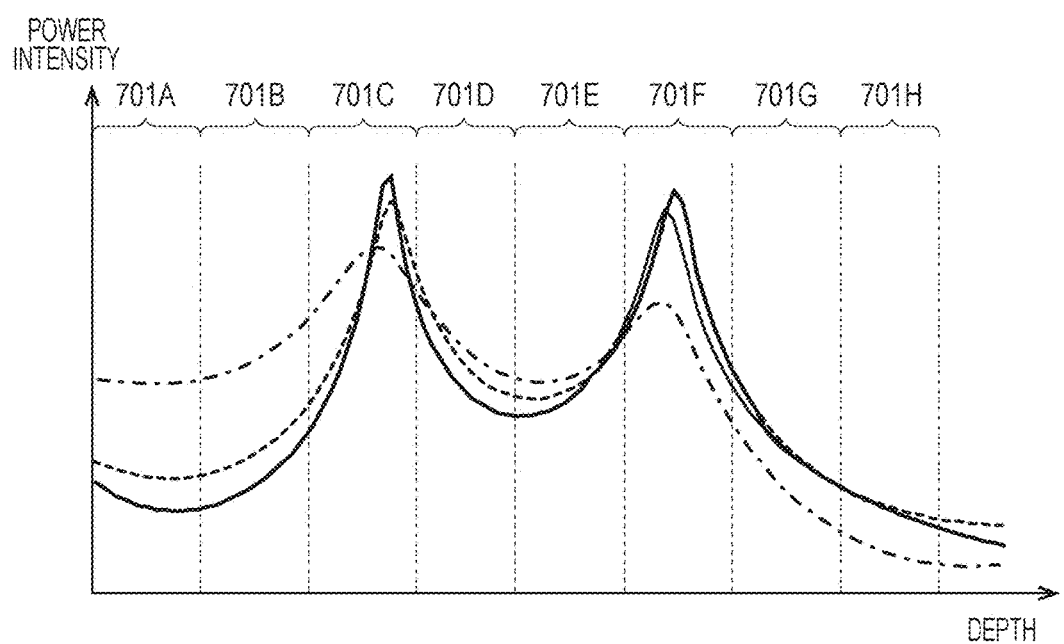
FIG. 8 is a graph obtained by extracting and plotting part of power intensity distributions obtained in a second embodiment.
Figure 9:
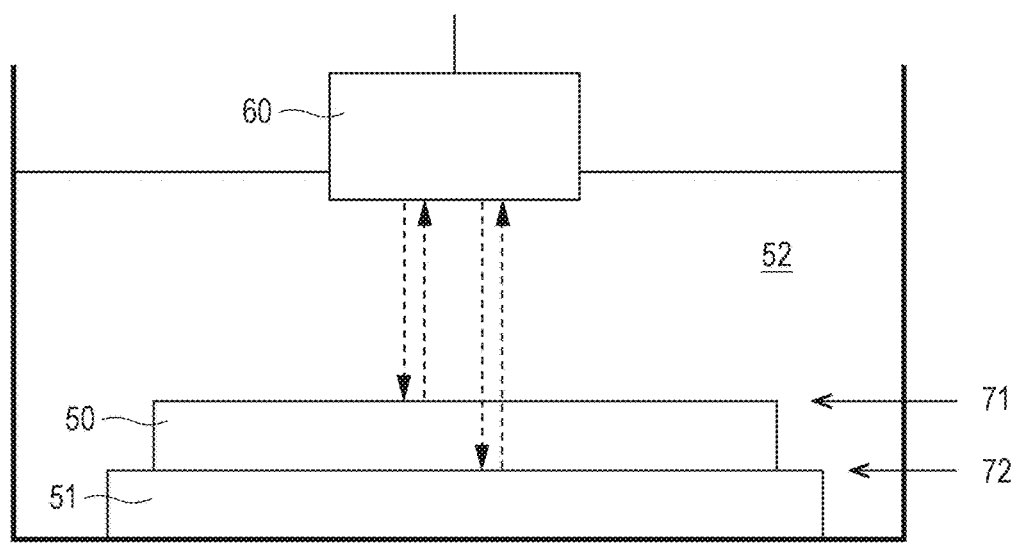
FIG. 9 is a diagram illustrating the configuration of an experiment apparatus for obtaining a reference signal described in PTL 1.

In S606, a combined power intensity distribution is generated using the partial power intensity distribution and the weight determined in each partial region. FIG. 8 illustrates an example of power intensity obtained by performing the above process. A plurality of power intensity distributions indicated by a thin solid line, a broken line, and a dash-dot line in FIG. 8 are the same as those illustrated in FIG. 7. These three power intensity distributions are combined to form a power intensity distribution indicated by a thick solid line illustrated in FIG. 8. As can be seen from this example, in the case of the combined power intensity distribution obtained in the present embodiment, the effect of improving the spatial resolution produced by the FDI method and the adaptive signal processing can be stably obtained by using a partial power intensity distribution that uses an appropriate reference signal in each partial region.

In the FDI method and the adaptive signal processing, the intensity of output power becomes higher as the waveform of a received signal and the waveform of a reference signal based on reflected waves received from a subject become more similar to each other, and power output from a position at which an object (a reflection interface or a reflection body) is located inside the subject is more likely to be an extremum. Therefore, by performing the process described in the present embodiment, it is possible to select a partial power intensity distribution that uses an appropriate reference signal in each partial region in an image capture region.

In addition, by weighting a plurality of partial power intensity distributions used around a partial region in which an extremum has not been particularly detected and by generating a combined power intensity distribution, it is possible to offer an image in which there are no considerable differences between the partial regions and that does not feel unnatural. Although a method for selecting a power intensity distribution having highest power intensity and an extremum has been described above, an extremum smaller than or equal to a certain value of power intensity need not be selected. In doing so, effects of noise components and the like can be suppressed, and a partial power intensity distribution that uses an appropriate reference signal in each partial region can be stably selected.

Thus, the FDI combining block 008 generates a combined power intensity distribution using a plurality of input power intensity distributions. The combined power intensity distribution generated by the FDI combining block 008 is output to the image processing block 010.

The image processing block 010 executes various types of image processing such as smoothing and edge reinforcement on the input combined power intensity distribution, and outputs brightness data to the image display unit 011. The image display unit 011 displays the input brightness data.

As described above, in the present embodiment, a reference signal corresponding to the shape of a subject within an image capture range can be used in each part of the image capture range in the FDI method and the adaptive signal processing. Therefore, the effect of improving the spatial resolution can be further enhanced and stably obtained. Although a plurality of partial regions are formed by dividing power intensity distributions on the same scan line, the same effect can be obtained by dividing power intensity distributions into regions having two-dimensional areas and by using these regions as partial regions instead.

Third Embodiment

The present invention can also be realized by executing the following process. That is, in this process, software (a program) that realizes the functions of each of the above-described embodiments is supplied to a system or an apparatus through a network or various storage media, and a computer (alternatively, a central processing unit (CPU) or microprocessor unit (MPU)) in the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-191415, filed Sep. 2, 2011, which is hereby incorporated by reference herein in its entirety.

REFERENCE SIGNS LIST

000 subject
001 probe
002 conversion element
003 transmission circuit
004 system control unit
005 reception circuit
006 delay and sum block
007 FDI adaptive processing block
008 FDI combining block
009 reference signal storage block
010 image processing block
011 image display unit
701A to 701H partial region

The invention claimed is:

1. A subject information obtaining apparatus that obtains information regarding a subject, the subject information obtaining apparatus comprising:
   a probe having a plurality of conversion elements;
   the plurality of conversion elements being configured to transmit an elastic wave to the subject and receive a reflected elastic wave and convert the received elastic wave into a plurality of received signals;
   a computing unit having a storage unit and a frequency-domain interferometry adaptive processing unit,
   the storage unit being configured to store a plurality of predetermined reference signals each representing a received signal of a wave from a known interface of an object with mutually different incident angles, radii of curvature, or sizes; and
   the frequency-domain interferometry adaptive processing unit being configured to execute a frequency-domain interferometry method and adaptive signal processing which adaptively applies weight on the plurality of received signals and two or more reference signals among the plurality of reference signals, to obtain a power intensity distribution for each of the two or more reference signals,
   wherein the obtained two or more power intensity distributions are indicative of a spatial resolution of the information regarding the subject.

2. The subject information obtaining apparatus according to claim 1, further comprising:
   a delay and sum unit configured to execute a delay and sum process using the plurality of received signals,
   wherein the frequency-domain interferometry adaptive processing unit executes the frequency-domain interferometry method and the adaptive signal processing using a plurality of signals after the delay and sum process output from the delay and sum unit and the two or more reference signals.

3. The subject information obtaining apparatus according to claim 1, further comprising:
   an output unit configured to output a power intensity distribution to be used to obtain the information regarding the subject using the two or more power intensity distributions,
   wherein the output unit outputs a combined power intensity distribution by executing a combining process using the two or more power intensity distributions or outputs a single power intensity distribution by selecting the power intensity distribution from among the two or more power intensity distributions with the highest spatial resolution.

4. The subject information obtaining apparatus according to claim 3, wherein the output unit outputs the combined power intensity distribution by averaging the two or more power intensity distributions.

5. The subject information obtaining apparatus according to claim 3,
wherein the output unit divides a region in which the two or more power intensity distributions are obtained into a plurality of partial regions, and
wherein, in the plurality of partial regions, the output unit outputs the combined power intensity distributions by, in a first partial region, in which there is a power intensity distribution having highest power intensity and an extremum among the two or more power intensity distributions, selecting the power intensity distribution having highest power intensity and an extremum as a partial power intensity distribution in the first partial region, and by, in a second partial region, in which there is no power intensity distribution having highest power intensity and an extremum among the two or more power intensity distributions, determining a power intensity distribution obtained by weighting and summing the two or more power intensity distributions to be the partial power intensity distribution in the first partial region.

6. The subject information obtaining apparatus according to claim 1, wherein the adaptive signal processing includes a Capon method, a MUSIC method, or a ESPRIT method.

7. A method for obtaining subject information by the subject information obtaining apparatus according to claim 1, the method comprising:
transmitting, using the plurality of conversion elements, the elastic wave to the subject;
receiving, using the plurality of conversion elements, the elastic wave reflected from an interface inside the subject;
executing, using the frequency-domain interferometry adaptive processing unit, a frequency-domain interferometry method and adaptive signal processing which adaptively applies weight on a plurality of received signals output from the plurality of conversion elements that have received the elastic wave and the two or more reference signals among the plurality of reference signals each representing a received signal of a wave from a known interface of an object with mutually different incident angles, radii of curvature, or sizes, to obtain a power intensity distribution for each of the two or more reference signals,
wherein the obtained two or more power intensity distributions are indicative of a spatial resolution of the information regarding the subject.

8. The method for obtaining subject information according to claim 7, further comprising:
executing, using the frequency-domain interferometry adaptive processing unit, a delay and sum process using the plurality of received signals,
wherein, in the step of obtaining the two or more power intensity distributions, the frequency-domain interferometry method and the adaptive signal processing are executed using a plurality of signals after the delay and sum process that have been subjected to the delay and sum process and the two or more reference signals.

9. The method for obtaining subject information according to claim 7, further comprising:

outputting, using an output unit, a power intensity distribution to be used to obtain the information regarding the subject using the two or more power intensity distributions,
wherein, in the step of outputting the power intensity distribution, a combined power intensity distribution is output by executing a combining process using the two or more power intensity distributions or by selecting a single power intensity distribution from among the two or more power intensity distributions with the highest spatial resolution.

10. The method for obtaining subject information according to claim 9, wherein, in the step of outputting the power intensity distribution, the combined power intensity distribution is output by averaging the two or more power intensity distributions.

11. The method for obtaining subject information according to claim 9,
wherein, in the step of outputting the power intensity distribution, a region in which the two or more power intensity distributions are obtained is divided into a plurality of partial regions,
wherein, in the plurality of partial regions, the combined power intensity distribution is output by, in a first partial region, in which there is a power intensity distribution having highest power intensity and an extremum among the two or more power intensity distributions, selecting the power intensity distribution having highest power intensity and an extremum as a partial power intensity distribution in the first partial region, and by, in a second partial region, in which there is no power intensity distribution having highest power intensity and an extremum among the two or more power intensity distributions, determining a power intensity distribution obtained by weighting and summing the two or more power intensity distributions to be the partial power intensity distribution in the first partial region.

12. The subject information obtaining method according to claim 7, wherein the adaptive signal processing includes a Capon method, a MUSIC method, or a ESPRIT method.

13. A non-transitory medium storing a program for causing a computer to execute: the steps included in the method for obtaining subject information according to claim 7.

14. A subject information obtaining apparatus comprising:
a plurality of conversion elements configured to emit an elastic wave and to generate a plurality of electric signals in response to a reception of an elastic wave;
a delay and sum unit configured to execute a delay and sum processing using the plurality of electric signals;
a storage unit configured to store a plurality of reference signals each representing a received signal of a wave from a known interface of an object with mutually different incident angles, radii of curvature, or sizes;
a signal processing unit; and
an output unit;
wherein the plurality of conversion elements transmits an elastic wave to the subject and generates a plurality of electric signals in response to a reception of an elastic wave reflected by an object within the subject;
the signal processing unit performs a frequency domain interferometry method and adaptive signal processing which adaptively applies weight on the plurality of electric signals that has been processed by the delay and sum unit and the plurality of reference signals, and obtains a plurality of power intensity distributions for each of the plurality of reference signals; and the output unit outputs either a combined power intensity distribution obtained by combining the plurality of power intensity distributions, or one of the plurality of power intensity distributions with the highest spatial resolution, wherein the plurality of power intensity distributions are indicative of a spatial resolution of information regarding the subject.

15. The subject information obtaining apparatus according to claim 14, wherein, when the output unit outputs the combined power intensity distribution, the output unit obtains the combined power intensity distribution by averaging the plurality of power intensity distributions.

16. The subject information obtaining apparatus according to claim 14, wherein the adaptive signal processing includes a Capon method, a MUSIC method, or a ESPRIT method.

* * * * *